(12) United States Patent
Freed

(10) Patent No.: US 7,951,073 B2
(45) Date of Patent: May 31, 2011

(54) ENDOSCOPIC DEVICE HAVING SPRAY MECHANISM AND RELATED METHODS OF USE

(75) Inventor: David I. Freed, Westborough, MA (US)

(73) Assignee: Boston Scientific Limited, Christ Church (BB)

( * ) Notice: Subject to any disclaimer, the term of this patent is extended or adjusted under 35 U.S.C. 154(b) by 1024 days.

(21) Appl. No.: 10/760,520

(22) Filed: Jan. 21, 2004

(65) Prior Publication Data

US 2005/0159648 A1 Jul. 21, 2005

(51) Int. Cl.
*A61B 1/12* (2006.01)
(52) U.S. Cl. ......... 600/159; 606/110; 606/113; 606/114
(58) Field of Classification Search ............... 606/110, 606/113–114; 600/159
See application file for complete search history.

(56) References Cited

U.S. PATENT DOCUMENTS

| | | | |
|---|---|---|---|
| 4,204,528 A * | 5/1980 | Termanini ................. 600/109 |
| 4,682,599 A | 7/1987 | Konomura |
| 5,098,440 A | 3/1992 | Hillstead |
| 5,176,688 A * | 1/1993 | Narayan et al. ............. 606/128 |
| 5,486,182 A | 1/1996 | Nakao et al. |
| 5,575,694 A | 11/1996 | Hawkins et al. |
| 5,599,324 A | 2/1997 | McAlister et al. |
| 5,846,248 A | 12/1998 | Chu et al. |
| 5,871,440 A * | 2/1999 | Okada ..................... 600/129 |
| 5,947,978 A | 9/1999 | Holsinger |
| 6,162,209 A * | 12/2000 | Gobron et al. ............... 606/1 |
| 6,375,661 B2 | 4/2002 | Chu et al. |
| 6,402,740 B1 | 6/2002 | Ellis et al. |
| 6,517,539 B1 * | 2/2003 | Smith et al. ................ 606/47 |
| 6,517,551 B1 * | 2/2003 | Driskill .................... 606/113 |
| 6,589,231 B1 | 7/2003 | Gobron et al. |
| 6,589,252 B2 * | 7/2003 | McGuckin, Jr. ............ 606/114 |
| 6,610,056 B2 | 8/2003 | Durgin et al. |
| 6,660,011 B2 * | 12/2003 | Levinson ................. 606/113 |
| 6,780,193 B2 * | 8/2004 | Leslie et al. .............. 606/114 |
| 6,960,182 B2 * | 11/2005 | Moutafis et al. ............ 604/43 |

\* cited by examiner

*Primary Examiner* — Matthew J Kasztejna
(74) *Attorney, Agent, or Firm* — Seager, Tufte & Wickhem, LLC

(57) ABSTRACT

Various embodiments of a surgical device that combines tissue cutting and spraying in a single device and related methods of use are disclosed. The device may include an elongated member having a proximal end and a distal end, an end effector proximate the distal end of the elongated member, and a nozzle member configured to substantially seal the distal end of the elongated member. The nozzle member may define a flow path in fluid communication between inside and outside of the elongated member when the distal end of the elongated member is sealed with the nozzle member.

95 Claims, 5 Drawing Sheets

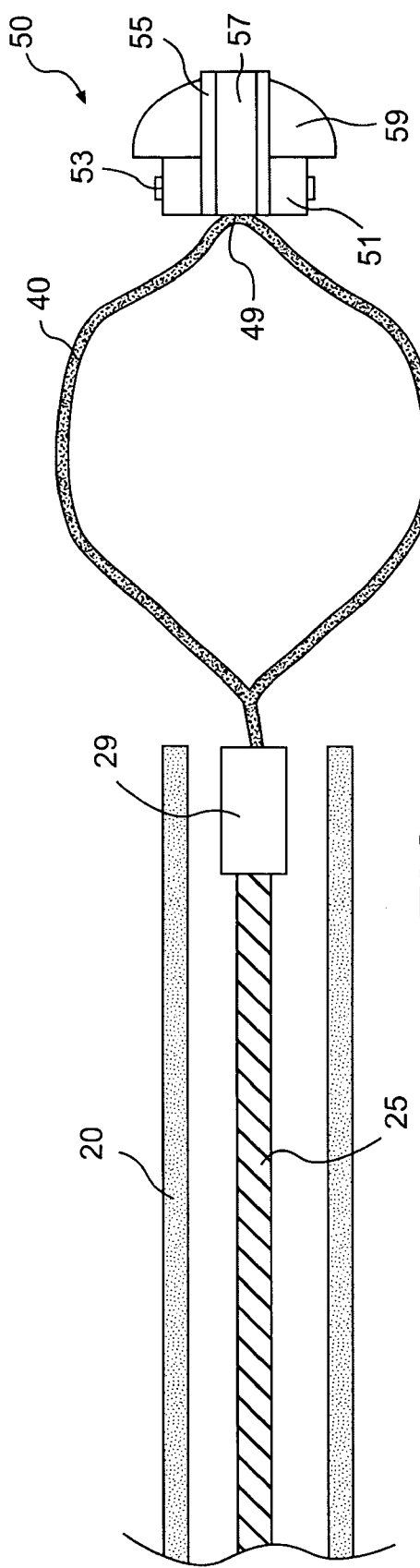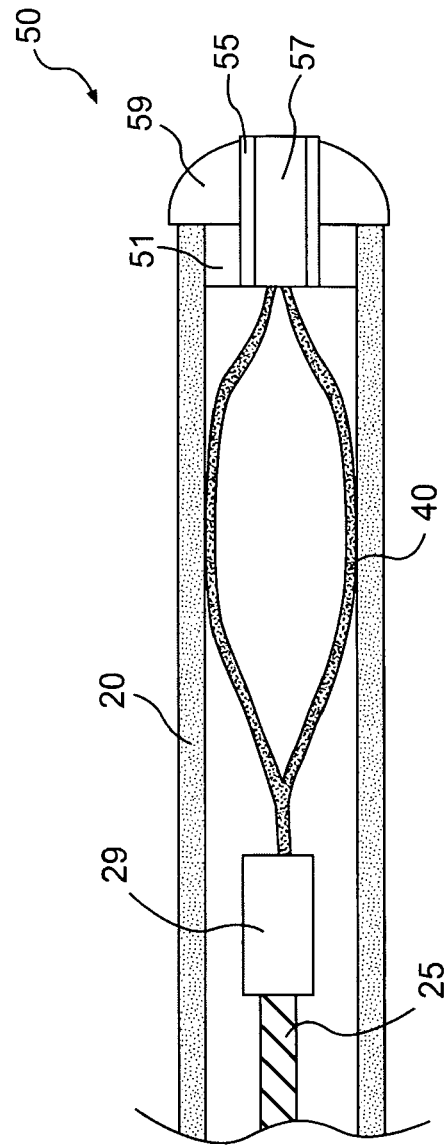

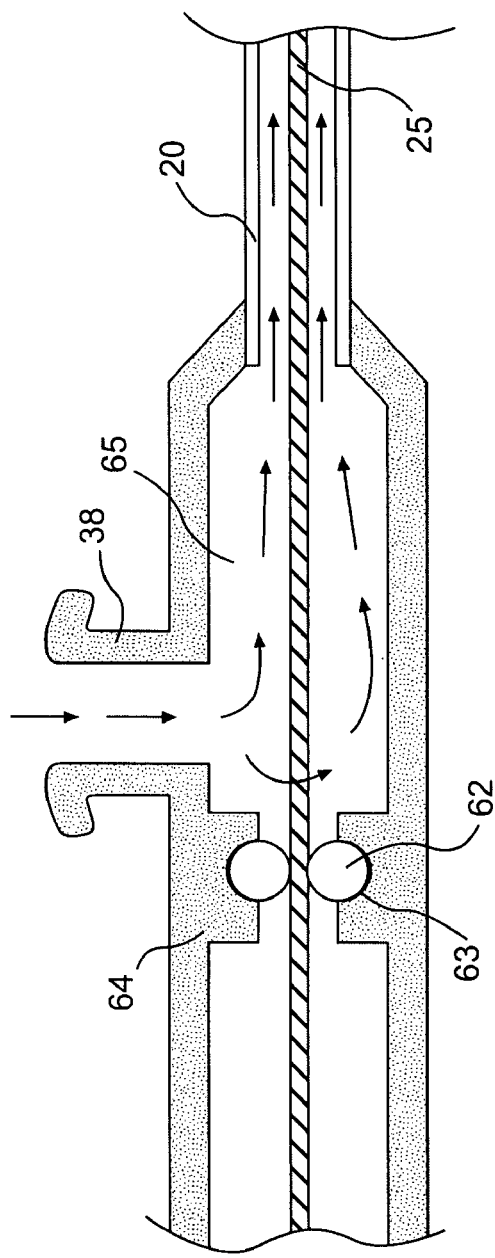

ENDOSCOPIC DEVICE HAVING SPRAY MECHANISM AND RELATED METHODS OF USE

DESCRIPTION OF THE INVENTION

1. Field of the Invention

Embodiments of the present invention relate to a surgical instrument having a spray mechanism and related methods of use. In a particular embodiment, the present invention relates to an endoscopic device that combines tissue cutting and spraying in a single device for use in, for example, a colonoscopic polypectomy.

2. Description of the Related Art

Colon cancer, including colorectal cancer, is one of the leading causes of cancer deaths. Despite advancements in therapeutic treatment techniques, the mortality rate from colon cancer remains high, and effective preventive measures for reducing the mortality are highly desired. As one of the preventive measures, it has been suggested that early detection and removal of adenomas (adenomatous polyps) during a routine colonoscopy effectively reduces the incidence of cancer because the adenoma-carcinoma sequence is believed to be the precursors for the vast majority of colon cancers.

Polypectomy is a therapeutic procedure typically used by a doctor to remove the adenomas from the colon or rectum. For example, once adenomas are detected during a routine colonoscopy or sigmoidoscopy, a doctor may insert a suitable polypectomy device, such as, for example, a snare catheter or biopsy forceps, to the site of the adenomas and remove the adenomas. However, while some of the adenomas are polypoid that are readily detectable, some adenomas are small sized, have a flat or depressed profile, or lack sufficient color contrast with respect to the surrounding mucosa, which render the detection of such adenomas extremely difficult and may require specialized techniques to detect them.

Recent studies indicate that the use of a dye agent, such as, for example, indigo carmine (indigotine, E132), used in contrast chromoscopy techniques, sprayed onto the colonic surface increases the detection of previously unvisualized adenomas. For this purpose, a specially designed spray catheter is passed through the endoscope to apply the dye agent directly onto the colonic surface. Once adenomas are detected, however, this procedure may require withdrawal of the spray catheter from the endoscope in order to insert an appropriate polypectomy device.

SUMMARY OF THE INVENTION

Therefore, an embodiment of the invention relates to an endoscopic device that can facilitate the above-mentioned procedure by combining the ability to perform polypectomy and dye spraying in a single device. Such an embodiment includes an endoscopic device having a spray mechanism integrally incorporated into the device, thereby eliminating the need for using a separate spray catheter.

To attain the advantages and in accordance with the purpose of the invention, as embodied and broadly described herein, one aspect of the invention may provide a medical device including a proximal handle, a distal assembly for performing a medical procedure, and an elongated member having a lumen and connecting the proximal handle to the distal assembly, where actuation of the proximal handle causes the distal assembly to perform the medical procedure. The distal assembly may include an end effector and a distal member defining a flow path therein for fluid communication between the lumen and an outside of the elongated member. The flow path may have a cross-sectional flow area less than a cross-sectional flow area of the lumen.

Another aspect of the present invention may provide a medical device including an elongated member having a proximal end, a distal end, and a lumen therethrough, an end effector proximate the distal end of the elongated member, and a nozzle member configured to substantially seal the distal end of the lumen. The nozzle member may define a flow path in fluid communication between the lumen and an outside of the elongated member when the distal end of the lumen is sealed with the nozzle member.

In yet another aspect of the present invention, a method of performing a medical procedure may be provided. The method includes inserting a medical device into a tissue tract of a patient, spraying fluid through a lumen of the medical device and onto tissue of the tissue tract to enhance visualization of tissue of the tissue tract, and actuating an end effector of the medical device to perform the medical procedure.

In still another aspect of the present invention, a method of performing a medical procedure may include inserting a medical device into a patient, where the medical device includes an elongated member having a lumen, an end effector proximate a distal end of the elongated member, and a distal member configured to substantially seal the distal end of the lumen. The nozzle member may define a flow path in fluid communication between the lumen and an outside of the elongated member when the lumen is sealed with the nozzle member. The method may further includes injecting fluid through the distal member of the medical device and actuating the end effector to perform the medical procedure.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings:

FIG. 5 is an exploded cross-sectional view of a distal portion of the snare catheter shown in FIGS. 1 and 2;

FIG. 6 is an exploded cross-sectional view of a distal portion of the snare catheter shown in FIGS. 3 and 4;

FIG. 7 is an exploded partial cross-sectional view of the proximal portion of the snare catheter shown in FIGS. 1–4, illustrating the fluid flow path from a fluid supply source to a tubular member of the catheter, according to an embodiment of the present invention;

FIGS. 8A and 8B are cross-sectional views of nozzle members, according to various embodiments of the present invention;

DESCRIPTION OF THE EMBODIMENTS

Figure 1:
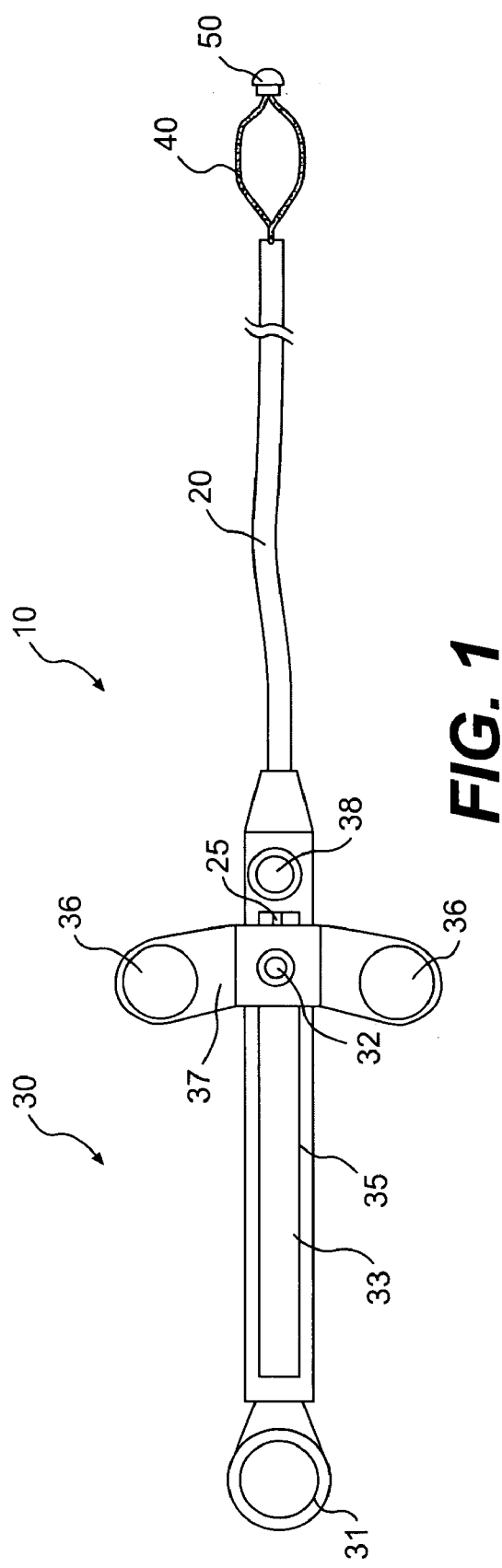
FIGS. 1 and 2 are top and side views of a snare catheter having a spray mechanism, according to an embodiment of the present invention, illustrating an open position of the snare catheter.

Reference will now be made in detail to the exemplary embodiments of the invention, examples of which are illustrated in the accompanying drawings. Wherever possible, the same reference numbers will be used throughout the drawings to refer to the same or like parts.

FIGS. 1–6 illustrate an endoscopic device 10 according to an exemplary embodiment of the present invention, which incorporates a spray mechanism integrally with a tissue acquisition or cutting device, such as, for example, a polypectomy snare catheter. While the present invention will be described in connection with a particular snare catheter, the present invention may be applied to, or used in connection with, any other types of snare catheters, numerous other tissue cutting end effector devices, such as biopsy forceps, jaws, or scissors, or other medical devices, including endoscopic medical devices, that may be used in combination with a spray mechanism. These include, but are not limited to, graspers, injection needles, hemostasis clips, and balloon dilation devices.

As best shown in FIGS. 1–4, the endoscopic device 10 may include an elongated flexible tubular member 20, a handle assembly 30, an end effector, such as snare loop 40, and a nozzle member 50 attached to a distal tip 49 (as shown in FIG. 5) of the snare loop 40. The device 10 may also include a flexible control member 25 extending between the handle assembly 30 and the snare loop 40 through a lumen of the tubular member 20. While the exemplary embodiment shown in FIGS. 1–4 includes the nozzle member 50, a device of the invention may not include the nozzle member 50, such that the fluid may exit the distal end of the tubular member 20 in a stream-like manner without a nozzle-induced spray effect.

The elongated flexible tubular member 20 may be fixedly secured to the handle assembly 30 via a suitable connection mechanism known in the art. The tubular member 30 may be made of a thermoplastic material, such as, for example, Teflon or PTFE, but other suitable material known in the art may also be used instead. The tubular member 20 may, for example, be a metal coil and may include suitable biocompatible coatings. The dimensions of the tubular member 20 may vary depending upon the type of procedure being performed. In an exemplary embodiment, the outer diameter and length of the tubular member range from 2.0 mm to 2.5 mm, and from 200 cm to 250 cm, respectively. The tubular member 20 preferably has sufficient flexibility to traverse tortuous anatomy.

The handle assembly 30 may include a thumb ring 31 fixedly attached to a main body 35. The assembly 30 may further include a movable member 37 having a suitable finger grip, such as, for example, a pair of finger rings 36. The main body 35 may be provided with a slide guide 33 along which the movable member 37 may reciprocally move relative to the main body 35 and the tubular member 20. The movable member 37 may also be configured to be rotatable with respect to the axis of the main body 35 so as to control the orientation of the snare loop 40 and/or the nozzle member 50. As will be described herein, this reciprocal movement of the movable member 37 controls the opening and closing of the snare loop 40.

The handle assembly 30 may include a fluid connector 38 which may be used to connect to a source of fluid 60 (see FIG. 4) intended to be sprayed by the device 10. Although the fluid connector 38 is shown to extend perpendicularly from the transverse axis of the handle assembly 30, any other types of connections known in the art may be employed. The fluid to be sprayed may be supplied by a suitable pressurizing means. For example, in an embodiment shown in FIG. 4, the fluid may be injected into the device 10 by a syringe 60, but any other suitable fluid supplying member may be alternatively used. The fluid connector 38 may include a suitable interlocking mechanism (not shown) associated with a fluid supplying member, such as a luer lock, so as to provide a leak-proof fluid connection between the device 10 and the fluid supplying member 60. Various seal members may also be provided to enhance the leak-proof fluid connection. When the fluid connector 38 is not in use, the fluid connector 38 may be provided with a stopper or cap (not shown) to close the opening of the connector 38.

The distal portion of the handle assembly 30 may include a fluid chamber 65 for temporarily storing the fluid injected from the fluid supplying member 60 and directing the fluid to the tubular member 20, as shown in FIG. 7. The fluid chamber 65 may be separated from the proximal portion of the handle assembly 30 by an annular flange 64 and a sealing member, such as, for example, a sealing ring 62, so that the fluid injected into the fluid chamber 65 does not penetrate into the proximal portion of the handle assembly 30. The annular flange 64 may form a circumferential groove 63 on an inner surface of the flange 64 to accommodate the sealing ring 62, thereby preventing axial movement of the sealing ring 62. Alternatively, the distal portion of the handle assembly 30 may include a tube extending from the fluid connector 38 to the proximal or distal end of the tubular member 20.

The handle assembly 30 may also include an electrical connector 32 for receiving cautery current from a power supply source (not shown) for an electrosurgical application. Other suitable electrical connectors, such as the embodiments described in U.S. Pat. No. 5,575,694 to Hawkins et al., entitled "Electrical Connector for Attachment to a Medical Device," the disclosure of which is hereby incorporated by reference, can also be used. The handle assembly 30 shown and described in FIGS. 1–4 is exemplary. Other handles known in the art that can actuate a distal end effector assembly and that also can include a fluid port may be used. For example, a handle assembly may also include a separate rotation actuator (not shown) for controlling a rotational movement of the snare loop 40 or may have a scissors-like actuation mechanism or different actuation mechanism for operating the snare loop 40.

The control member 25, such as, for example, a single filament or multifilament shaft or wire, may be flexible enough to pass through a tortuous body cavity, yet sufficiently stiff to resist minor compressive force, thereby permitting axial movement of the control member 25 relative to the tubular member 20. For this purpose, the device 10 may optionally include an inner sleeve (not shown) fixedly secured to the movable member 37 of the handle assembly 30 and configured to move together with the control member 25. The sleeve may be formed of a thermoplastic material, such as, for example, Nylon or Polyethylene, or a metal, such as, for example, stainless steel. In an exemplary embodiment, the control member 25 may be made of stainless steel, nickel-titanium alloy, or a combination of the two, but any other suitable material known in the art may also be used. In another exemplary embodiment, at least a portion of the control member 25 or sleeve may be coated with a lubricating material to facilitate the axial movement of the control member 25.

The distal end of the control member 25 may be connected to the snare loop 40 via a suitable connector, such as a crimp ring 29, so as to move the snare loop 40 in and out of the tubular member 20 to open and close the snare loop 40. Alternatively, As best shown in FIGS. 5 and 6, the snare loop 40 can be opened by extending the loop 40 distally out of the tubular member 20 and closed by retracting the snare loop 40 into the tubular member 20. Since the control member 25 may be coupled to the movable member 37 of the handle assembly 30 via a suitable coupling member, such as, for example, a rigid tube, the opening and closing operations of the snare loop 40 may be controlled by reciprocating the movable member 37 relative to the main body 35 and the tubular member 20. In an alternative exemplary embodiment, the control member 25 may itself form a snare loop 40 at its distal end, instead of attaching a separate snare loop 40.

The snare loop 40 may be formed of an elastic material, such as, for example, stainless steel, nickel-titanium alloy, or any other materials that exhibit sufficient restorability of its original shape. The snare loop 40 may be formed of a single filament or braided multifilament wire. The size and shape of the snare loop 40 may vary significantly depending on the types and orientation of the polyps for which the device is used. In various exemplary embodiments, the snare loop 40 may have an oval shape, hexagonal shape, duck-bill shape, crescent shape, or any other shape known in the art. Optionally, at least a portion of the loop may be angled to facilitate removal of certain types of polyps.

The nozzle member 50, according to an exemplary embodiment of the invention, is best shown in FIGS. 5 and 6. The nozzle member 50 may be fixedly attached to a distal tip portion 49 of the snare loop 40. Alternatively, the nozzle member 50 may be removably attached to the snare loop 40 and, if spraying of the fluid is not desired, the nozzle member 50 may be detached from the snare loop 40.

The nozzle member 50 may include a base portion 51 and a head portion 59. The base portion 51 may have an outer diameter slightly less than the inner diameter of the tubular member 20, so that the nozzle member 50 may be fit into the distal end portion of the tubular member 20. In an alternative embodiment, the outer diameter of the base 51 may be equal to or greater than the inner diameter of the tube 20. Optionally, the base portion 51 may be provided with a suitable sealing member, such as, for example, a resilient sealing ring 53, to provide leak-tight engagement between the nozzle member 50 and the distal end of the tubular member 20. In an alternative embodiment, the base portion 51 may form a frusto-conical shape for enhanced engagement with the tubular member 20. The head portion 59, preferably formed integrally with the base portion 51, may have a smooth outer profile, such as, for example, a hemi-spherical configuration, for ease of insertion through an endoscope lumen and a patient's tissue tract. The outer diameter of the head portion 59 may be substantially equal to or greater or less than the inner diameter of the tubular member 20.

The nozzle member 50 may include at least one internal flow path 55 for injecting the fluid flowed to the distal end of the tubular member 20. For example, as shown in FIGS. 5 and 6, the nozzle member 50 may include at least one through-hole 55 or an annular passage for spraying the fluid. Due to its smaller flow area relative to the flow area of the tubular member 20, the nozzle member 50 may create a sufficient differential pressure across the inlet and outlet of the flow path 55, thereby functioning as a spray nozzle for spraying the fluid. If the flow path is formed of an annular passage 55, the nozzle member 50 may include at least one supporting rib for structurally supporting the center piece 57 to the rest of the nozzle member 50.

Alternatively or additionally, the nozzle member 50 may include a plurality of small diameter non-annular passages therethrough, or any other suitable number and type of passages through nozzle member 50.

In addition, the cross-sectional area of the flow path in the nozzle member 50 may be varied along the length of the flow path 155 depending on the desired fluid-dynamic effect. For example, as shown in FIGS. 8A and 8B, a nozzle member 150, 250 may have various configurations for the internal flow path 155, 255. In an embodiment shown in FIG. 8A, the internal flow path 155 is varied to create a nozzle-diffuser configuration where the annular flow path at the inlet 151 is converged at a portion 154 of the flow path 155 and diverged gradually therefrom to the exit 159, thereby enhancing the spraying effect of the fluid. Alternatively, as show in FIG. 8B, the internal flow path 255 may have a shower head configuration at the exit 259, so that the fluid may be sprayed in a shower-like manner.

Figure 2:
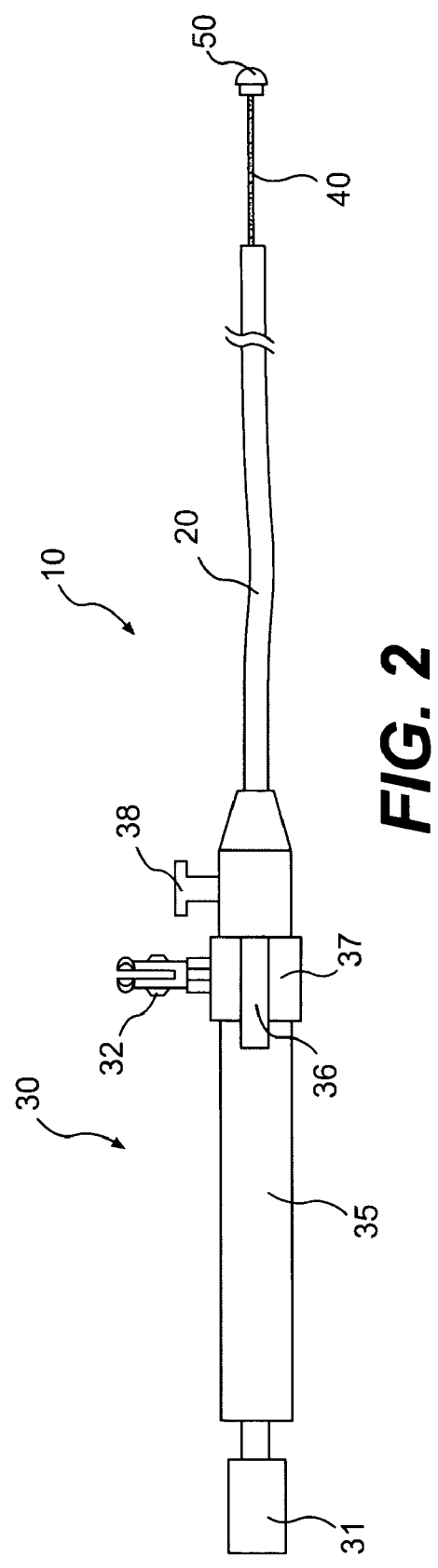
Figure 3:
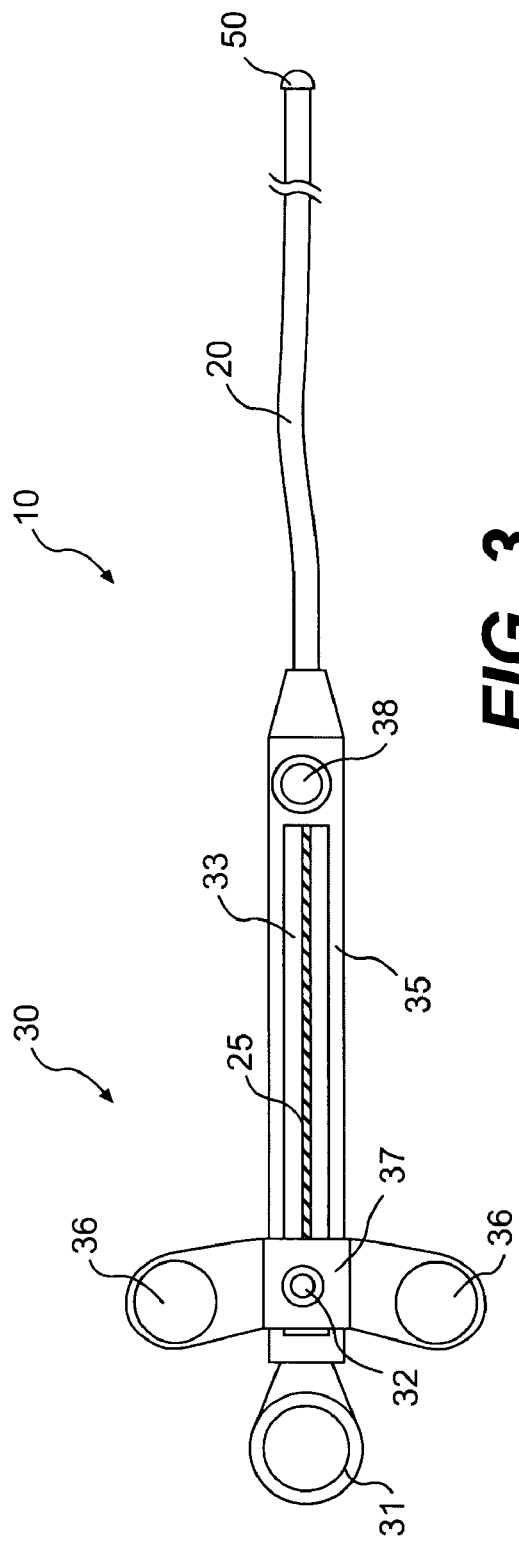
FIGS. 3 and 4 are top and side views of the snare catheter shown in FIG. 1, illustrating a closed position of the snare catheter.
Figure 4:
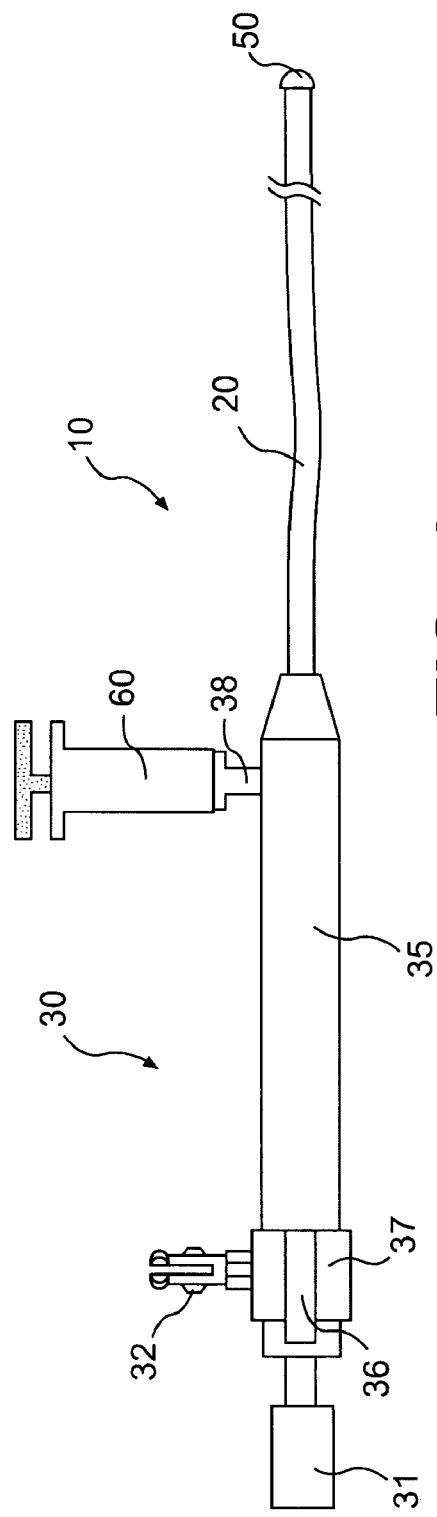

The operation of the device will be described in detail with reference to FIGS. 1–7. FIGS. 3, 4, and 6 show a closed position of the snare loop 40. To attain this position, the movable member 37 may be moved proximally relative to the main body 35 to retract the snare loop 40 inside the tubular member 20, causing the snare loop 40 to close. As best shown in FIG. 6, the nozzle member 50 may then be snuggly received at the distal end portion of the tubular member 20, ready for spraying the fluid.

This closed position of the snare loop 40 may be the preferred position while inserting the device 10 into the body. With this position of the snare loop 40, the device 10 may be inserted into an endoscope lumen to position the distal end of the device 10 near the tissue site. A suitable imaging device, such as, for example, an endoscope, colonoscope, or sigmoidoscope, may be used to aid in positioning the distal end of the device 10. Once the distal end of the device 10 is properly positioned, the fluid supplying member 60 may be actuated to supply, for example, a suitable dye or radiographic contrast agent through the fluid connector 38. Upon actuation of the fluid supplying member 60, the fluid may pass through the fluid chamber 65 of the handle assembly 30 and through the tubular member 20, as indicated by the arrows in FIG. 7. The fluid may then be sprayed by passing through the nozzle member 50 disposed at the distal end of the tubular member 20 to aid in visualization of the tissue site.

With the enhanced visualization of the tissue site, the operator may perform a suitable surgical procedure, such as, for example, a polypectomy procedure, with the device 10 without requiring withdrawal of the device 10 from the tissue site. FIGS. 1, 2, and 5 show an open position of the snare loop 40, which may be used to perform such a polypectomy procedure. To attain this position, the movable member 37 may be moved distally relative to the main body 35 to extend the snare loop 40 beyond the distal end of the tubular member 20, causing the snare loop 40 to open. In this position, the device 10 may be manipulated appropriately to receive tissue in the snare loop 40. The nozzle member 50 in this position may not serve any function nor interfere with the operation of the polypectomy procedure. It should be understood, however, that it may be possible, if desired, to inject the fluid through the tubular member 20 in this open position. But, since the nozzle member is no longer associated with the tubular member 20, the fluid may not have a nozzle-like effect.

Once the tissue is received in the snare loop 40, the movable member 37 may be moved proximally relative to the main body 35 to retract the snare loop 40 inside the tubular member 20 to cause the snare loop 40 to close, severing the tissue received in the snare loop 40. The operator may repeat any portion of the medical procedure described above, in any order, as desired. For example, the operator may repeat the step of spraying fluid before, during, or after a given medical procedure, with the same fluid or with any other fluid.

Although the present invention was described in connection with a particular polypectomy procedure, the present invention may be applied to, or used in connection with, any other surgical procedures that involve injection of a fluid. For example, instead of spraying the dye agent for the visualization purpose, any other fluids, such as, for example, irrigation fluid, therapeutic agent, or other suitable treatment agents, may alternatively or additionally be sprayed, depending on the desired medical procedure.

Figure 9:
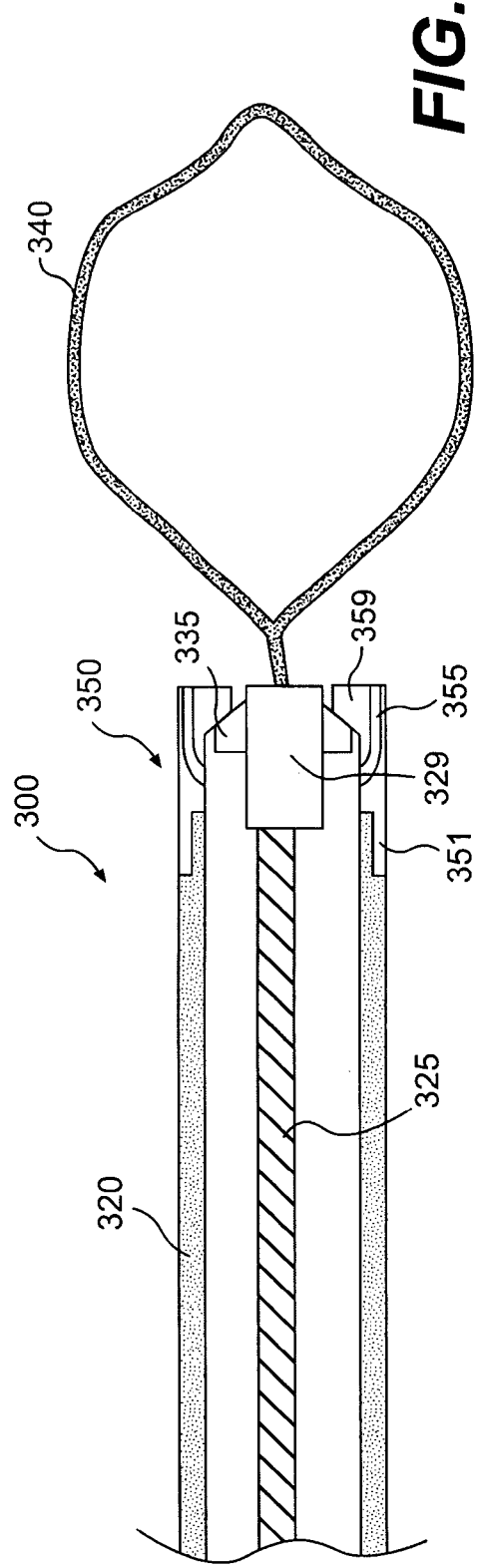
FIG. 9 is an exploded partial cross-sectional view of a distal portion of a snare catheter, according to another embodiment of the present invention.

FIG. 9 illustrates an endoscopic device 300 according to another exemplary embodiment of the present invention. In this embodiment, a nozzle member 350 may be fixedly secured to the distal end portion of the tubular member 320 and, thereby, the fluid may be sprayed when the snare loop 340 is in an open position. The nozzle member 350 may have a stepped proximal portion 351 to facilitate securing of the nozzle member 350 onto the tubular member 320. Any suitable securing mechanism, such as, for example, welding, crimping, gluing, etc., may be used to secure the nozzle member 350 onto the tubular member 320. Alternatively, the nozzle member 350 may be formed integrally with the tubular member 320.

At least one flow path 355 may be formed internally inside the nozzle member 350. In the exemplary embodiment shown in FIG. 9, the flow path 355 connects between the lumen of the tubular member 320 and the front surface of the tubular member 320. Other various arrangements for the flow path 355, including those similar to the embodiments described with reference to FIGS. 5, 8A, and 8B, may also be used instead. The nozzle member 350 may include a sealing member, such as, for example, an annular flange 359, which cooperates with a corresponding sealing member 335 formed on the outer surface of a connecting member 329 that connects a snare loop 340 and the control member 325. In an embodiment in which the control member 325 also forms the snare loop 340, a suitable sealing member having a similar configuration may be used. The sealing members 359, 335 may engage in a leak-proof manner so that the fluid may flow only through the flow path 355 formed inside the nozzle member 350. Any suitable handle assembly, including the handle assembly 30 described with reference to FIGS. 1–4, may be used and, thereby, detailed description of the handle assembly is omitted.

In operation, the device 300 may be inserted into an endoscope lumen to position the distal end of the device 300 near the tissue site. The closed position of the snare loop 340 may be the preferred position while inserting the device 300 into the body. Once the distal end of the device 300 is properly positioned, the snare loop 340 may be extended distally out of the tubular member 320 to open the snare loop 340, as shown in FIG. 9. In this open position, the annular flange 359 of the nozzle member 350 may cooperate with the sealing member 335 of the connecting member 329 so as to seal the distal end of the tubular member 335 and leave the flow path 355 formed inside the nozzle member 350 in fluid communication between the inside and outside of the tubular member 320.

A suitable fluid, such as, for example, a dye or radiographic contrast agent, may then be supplied to the distal end portion of the tubular member 320 and may be sprayed through the flow path 355 of the nozzle member 350 at the distal end of the tubular member 320. While the open position of the snare loop 340 is the preferred position for spraying, the fluid may also be injected when the snare loop 340 is in the closed position. For example, the nozzle member 350 may permit a fluid flow through an opening formed by the annular flange 359 in the closed position. Preferably, the restriction in the opening by the annular flange 359 may create a sufficient nozzle effect across the opening so that the fluid may be sprayed while passing through the opening.

Once the suitable fluid is sprayed, the snare loop 340 may be further manipulated to perform a desired surgical procedure, independent of the spraying operation. For example, the snare loop 340 may receive tissue therein and be retracted inside the snare loop 340 to sever the tissue received. Since the nozzle member 350 is not directly associated with the snare loop 340, the nozzle member 350 does not interfere with the operation of the snare loop. The operator may repeat any portion of the medical procedure described above, in any order, if desired. For example, the operator may repeat the step of spraying fluid before, during, or after the medical procedure with the same fluid or with any other suitable fluid.

Figure 10:
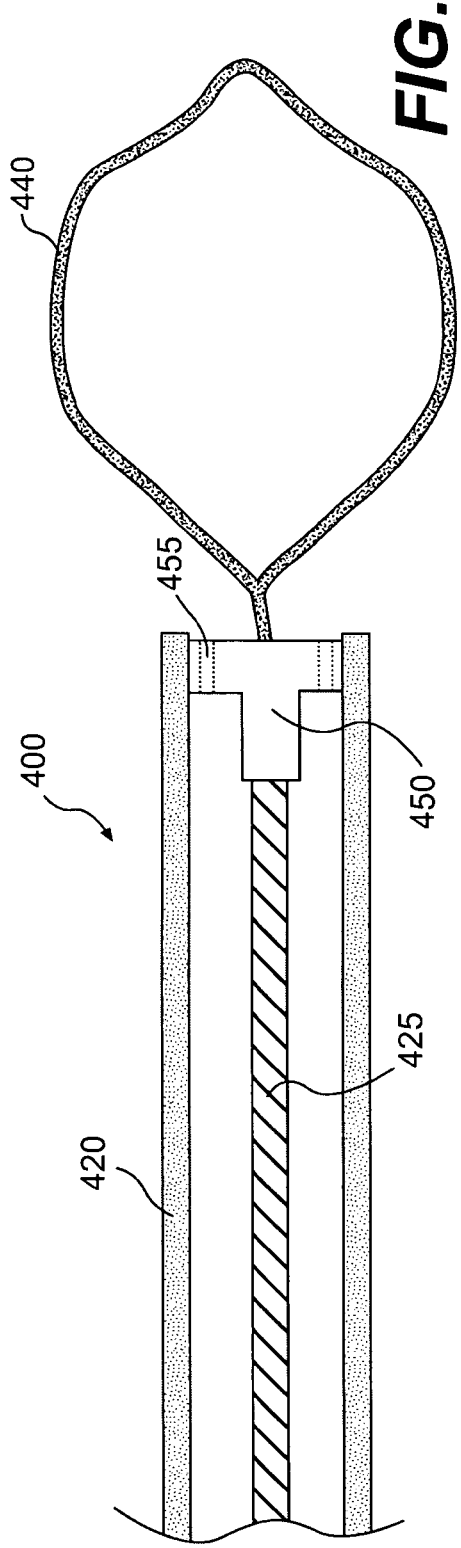
FIG. 10 is an exploded cross-sectional view of a distal portion of a snare catheter, according to still another embodiment of the present invention.

FIG. 10 illustrates an endoscopic device 400 according to still another exemplary embodiment of the present invention. In this embodiment, a connector 450 between the snare loop 440 and the control member 425 may form a nozzle member 450. The nozzle member 450 may have a plunger-like shape with a plate member at either a proximal or distal end (shown at the distal end of the nozzle member 450 in FIG. 10). The nozzle member 450 has at least one through-hole 455 through which the fluid may be sprayed. The nozzle member 450 may also have a sealing member (not shown) adjacent the surface in contact with the tubular member 420, so as to seal the opening of the tubular member 420 except the through-hole 455.

The device 400 may have a stop member (not shown) at the distal end portion of the tubular member 420, so that the nozzle member 450 may not move beyond the distal end of the tubular member 420. Alternatively or additionally, a handle assembly may have a suitable limiting mechanism for limiting the axial movement of the nozzle member 450. Optionally or in alternative, limiting the axial movement of the nozzle member 450 may be achieved by having the control member 425 with a predetermined length configured not to extend beyond the distal end of the tubular member 420. The device 400 may be operated in any suitable manner, including the operation described above with reference to FIG. 9, and, thereby, detailed description of the operation is omitted.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a proximal handle;
   an elongated member having a proximal end, a distal end, and a lumen therebetween, the proximal end being coupled to the proximal handle, the elongated member being sufficiently flexible to traverse through tortuous anatomy of a patient's body;

an end effector consisting essentially of a snare loop proximate the distal end of the elongated member, actuation of the proximal handle causing the snare loop to sever tissue; and a distal member configured to open and substantially close the distal end of the lumen, the distal member defining a flow path such that, when the distal member substantially closes the distal end of the lumen, the flow path enables a flow communication between the lumen and an outside of the elongated member.

2. The device of claim 1, wherein the flow path defined by the distal member has a cross-sectional flow area less than a cross-sectional flow area of the lumen.

3. The device of claim 1, wherein the handle includes a port in fluid communication with the lumen.

4. The device of claim 3, further comprising a fluid supplying member for supplying fluid to the port.

5. The device of claim 4, wherein the port includes an interlocking member configured to engage with the fluid supplying member.

6. The device of claim 4, wherein the fluid supplying member includes a syringe.

7. The device of claim 3, wherein the handle defines a fluid chamber sealed from a portion of the handle and for providing a passage of fluid from the port to the lumen.

8. The device of claim 1, wherein the distal member includes a sealing member to seal the lumen.

9. The device of claim 1, wherein at least a portion of the distal member has a frusto-conical shape for substantially closing the lumen.

10. The device of claim 1, wherein the distal member includes a base portion and a head portion, the base portion having an outer diameter substantially the same as an inner diameter of the lumen, the head portion having an outer diameter greater than the inner diameter of the lumen.

11. The device of claim 1, wherein the distal member includes a plate member having an outer diameter substantially the same as the inner diameter of the lumen.

12. The device of claim 1, wherein the flow path of the distal member has a varying cross-sectional flow area along the flow path.

13. The device of claim 12, wherein at least a portion of the flow path has a cross-sectional flow area smaller than that of at least one of an inlet and an outlet of the flow path.

14. The device of claim 1, wherein the distal member connects to the end effector.

15. The device of claim 14, wherein the distal member connects to the end effector at a distal end of the end effector.

16. The device of claim 15, wherein the distal member is movable relative to the lumen and is configured to substantially close the lumen when the end effector retracts proximally into the lumen and to open the lumen when the end effector extends distally out of the lumen.

17. The device of claim 1, wherein the distal member fixedly connects to the end effector at a proximal end of the end effector.

18. The device of claim 17, wherein the distal member includes a main body connected to the proximal end of the end effector and an annular flange extending from an outer surface of the main body, wherein the annular flange has an outer diameter substantially the same as the inner diameter of the elongated member.

19. The device of claim 18, wherein the flow path is formed in the annular flange.

20. The device of claim 1, wherein the distal member includes:

a main body fixedly connected to a proximal end of the end effector; and an annular body fixed to the distal end of the elongated member.

21. The device of claim 20, wherein the annular body includes a first portion extending internally from an inner surface of the annular body.

22. The device of claim 21, wherein the main body and the first portion are configured to contact each other to substantially close the lumen of the elongated member.

23. The device of claim 20, wherein the flow path has an inlet opening in a direction transverse to an axis of the annular body and an outlet opening in a direction substantially parallel to the axis of the annular body.

24. The device of claim 20, wherein the annular body has a stepped portion for securing the annular body to the elongated member.

25. The device of claim 1, wherein the handle includes a stationary part and a movable part movable relative to the stationary part.

26. The device of claim 25, wherein movement of the movable part relative to the stationary part causes the distal member to sealingly engage the distal end of the lumen so that the lumen is in fluid communication with the outside of the elongated member via the flow path of the distal member.

27. The device of claim 26, further comprising a control member having a proximal end coupled to the movable part and a distal end coupled to the end effector so that actuation of the movable part relative to the stationary part enables movement of the end effector to sever tissue.

28. The device of claim 1, wherein the handle includes an electrical connector for receiving cautery current from a power supply source.

29. The device of claim 28, wherein the electrical connector is electrically connected to the end effector.

30. The device of claim 1, wherein the distal member defines a plurality of flow paths.

31. The device of claim 1, wherein
the distal member comprises:
a main body connected to a proximal end of the end effector; and
an annular body fixed to the distal end of the elongated member, and
wherein the main body and the annular body are configured to contact each other to substantially close the distal end of the lumen.

32. The device of claim 31, wherein the annular body includes a first portion extending internally from an inner surface of the annular body.

33. The device of claim 32, wherein the main body and the first portion are configured to contact each other to substantially close the lumen of the elongated member.

34. The device of claim 31, wherein the flow path has an inlet opening in a direction transverse to an axis of the annular body and an outlet opening in a direction substantially parallel to the axis of the annular body.

35. The device of claim 1, wherein the end effector consists of a snare loop.

36. A medical device comprising:
an elongated member having a proximal end, a distal end, and a lumen therethrough, the elongated member being sufficiently flexible to traverse through a tortuous anatomy of a patient's body;
an end effector consisting essentially of a snare loop proximate the distal end of the elongated member, said end effector configured to sever tissue; and a nozzle member configured to substantially seal the distal end of the lumen, the nozzle member defining a flow path in fluid communication between the lumen and an outside of the elongated member when the distal end of the lumen is sealed with the nozzle member.

37. The device of claim 36, wherein the flow path has a flow area that is smaller than a flow area of the lumen.

38. The device of claim 36, further comprising a handle proximate the distal end of the elongated member and including a port.

39. The device of claim 36, wherein the nozzle member is configured to selectively seal the distal end of the lumen.

40. The device of claim 36, wherein the nozzle member connects to the end effector.

41. The device of claim 40, wherein the nozzle member connects to the end effector at a distal end of the end effector.

42. The device of claim 40, wherein the nozzle member connects to the end effector at a proximal end of the end effector.

43. The device of claim 36, wherein the nozzle member comprises a first member fixedly connected to a proximal end of the end effector and a second member fixedly connected to a distal end of the elongated member, wherein the first and second members are configured to contact one another so as to substantially seal the distal end of the lumen.

44. The device of claim 36, further comprising a handle proximate the proximal end of the elongated member, the handle configured to control movement of the end effector and the nozzle member relative to the elongated member.

45. The device of claim 44, further comprising a control member extending between the handle and at least one of the end effector and the nozzle member.

46. The device of claim 44, wherein the handle includes a connector for receiving cautery current from a power supply source, the connector electrically connected to the end effector.

47. The device of claim 36, wherein the nozzle member defines a plurality of flow paths.

48. The device of claim 36, wherein the end effector consists of a snare loop.

49. A method of performing a medical procedure, the method comprising:
    inserting a medical device into a tissue tract of a patient, the medical device comprising a lumen and a nozzle member configured to substantially seal a distal end of the lumen, the nozzle member defining a flow path in fluid communication between the lumen and an outside of the lumen when the distal end of the lumen is sealed with the nozzle member, the medical device further comprising an end effector consisting essentially of a snare loop coupled to the nozzle member;
    closing the distal end of the lumen with the nozzle member;
    spraying fluid through the flow path of the nozzle member and onto tissue of the tissue tract to enhance visualization of tissue of the tissue tract; and
    actuating the end effector of the medical device to sever the tissue of the tissue tract.

50. The method of claim 49, further comprising inserting an endoscope for viewing the tissue tract.

51. The method of claim 49, wherein the medical procedure is a colonoscopic polypectomy procedure.

52. The method of claim 49, further comprising supplying fluid to the medical device.

53. The method of claim 49, wherein spraying fluid includes spraying a chromoscopic dye agent.

54. The method of claim 49, wherein spraying fluid includes spraying a radiographic contrast agent.

55. The method of claim 49, further comprising supplying cautery current to the end effector.

56. The method of claim 49, wherein the nozzle member connects to the end effector.

57. The method of claim 49, wherein the nozzle member is fixedly connected to a distal end of the lumen.

58. The method of claim 49, wherein the medical procedure includes removing tissue from the tissue tract.

59. The method of claim 49, wherein at least a portion of the flow path in the nozzle member has a cross-sectional flow area smaller than both a cross-sectional flow area of an inlet of the flow path and a cross-sectional flow area of an outlet of the flow path.

60. The method of claim 49, wherein the nozzle member is fixedly connected to a proximal end of the end effector.

61. The method of claim 49, wherein the nozzle member includes a main body connected to a proximal end of the end effector and an annular body fixed to the distal end of the lumen.

62. The method of claim 61, wherein the annular body includes a first portion extending internally from an inner surface of the annular body and being configured to contact a portion of the main body to substantially close the lumen of the elongated member.

63. The method of claim 49, wherein the end effector consists of a snare loop.

64. A method of performing a medical procedure, the method comprising:
    inserting a medical device into a patient, the medical device comprising:
    an elongated member having a proximal end, a distal end, and a lumen therethrough, the distal end extending into the patient;
    an end effector consisting essentially of a snare loop proximate the distal end of the elongated member; and
    a distal member coupled to the end effector and configured to substantially seal the distal end of the lumen, the distal member defining a flow path in fluid communication between the lumen and an outside of the elongated member when the lumen is sealed with the distal member;
    injecting fluid through the distal member of the medical device; and
    actuating the end effector to sever tissue of a tissue tract.

65. The method of claim 64, further comprising injecting fluid through the lumen of the medical device when the lumen is not sealed with the distal member.

66. The method of claim 64, wherein:
    inserting the medical device includes inserting the medical device into the tissue tract of a patient;
    injecting fluid includes injecting a contrast agent for enhancing visualization of tissue in the tissue tract; and
    actuating the end effector includes removing tissue from the tissue tract.

67. The method of claim 64, further comprising inserting an endoscope for viewing the tissue tract.

68. The method of claim 64, further comprising supplying fluid to the lumen of the medical device.

69. The method of claim 64, further comprising supplying cautery current to the end effector.

70. The method of claim 64, wherein the flow path of the distal member has a flow area that is smaller than a flow area of the lumen.

71. The method of claim 64, wherein the distal member connects to the end effector.

72. The method of claim 64, wherein the distal member is fixedly connected to the distal end of the elongated member.

73. The method of claim 64, wherein at least a portion of the flow path has a cross-sectional flow area smaller than both a cross-sectional flow area of an inlet of the flow path and a cross-sectional flow area of an outlet of the flow path.

74. The method of claim 64, wherein the distal member is fixedly connected to a proximal end of the lumen.

75. The method of claim 64, wherein the distal member includes a main body connected to a proximal end of the end effector and an annular body fixed to the distal end of the elongated member.

76. The method of claim 75, wherein the annular body includes a first portion extending internally from an inner surface of the annular body and being configured to contact a portion of the main body to substantially close the lumen of the elongated member.

77. The method of claim 64, wherein the end effector consists of a snare loop.

78. A medical device comprising:
- a proximal handle;
- an elongated member having a proximal end, a distal end, and a lumen therebetween, the proximal end being coupled to the proximal handle, the elongated member being sufficiently flexible to traverse through tortuous anatomy of a patient's body;
- an end effector proximate the distal end of the elongated member, actuation of the proximal handle causing the end effector to perform a medical procedure; and
- a distal member configured to open and substantially close the distal end of the lumen, the distal member defining a flow path such that, when the distal member substantially closes the distal end of the lumen, the flow path enables a flow communication between the lumen and an outside of the elongated member,
- wherein at least a portion of the flow path has a cross-sectional flow area smaller than both a cross-sectional flow area of an inlet of the flow path and a cross-sectional flow area of an outlet of the flow path.

79. The device of claim 78, wherein the handle includes a port in fluid communication with the lumen.

80. The device of claim 78, wherein the end effector comprises a tissue cutting end effector.

81. The device of claim 80, wherein the end effector consists essentially of a snare loop.

82. The device of claim 78, wherein the distal member includes a base portion and a head portion, the base portion having an outer diameter substantially the same as an inner diameter of the lumen, the head portion having an outer diameter greater than the inner diameter of the lumen.

83. The device of claim 78, wherein the distal member includes a plate member having an outer diameter substantially the same as the inner diameter of the lumen.

84. The device of claim 78, wherein the distal member connects to the end effector at a distal end of the end effector.

85. The device of claim 84, wherein the distal member is movable relative to the lumen and is configured to substantially close the lumen when the end effector retracts proximally into the lumen and to open the lumen when the end effector extends distally out of the lumen.

86. The device of claim 78, wherein the distal member connects to the end effector at a proximal end of the end effector.

87. The device of claim 86, wherein the distal member includes a main body connected to the proximal end of the end effector and an annular flange extending from an outer surface of the main body, wherein the annular flange has an outer diameter substantially the same as the inner diameter of the elongated member.

88. The device of claim 78, wherein the distal member includes a main body connected to a proximal end of the end effector and an annular body fixed to the distal end of the elongated member.

89. The device of claim 88, wherein the annular body includes a first portion extending internally from an inner surface of the annular body and being configured to contact a portion of the main body to substantially close the lumen of the elongated member.

90. The device of claim 88, wherein the flow path has an inlet opening in a direction transverse to an axis of the annular body and an outlet opening in a direction substantially parallel to the axis of the annular body.

91. The device of claim 78, wherein the handle includes an electrical connector for receiving cautery current from a power supply source.

92. The device of claim 78, wherein the distal member defines a plurality of flow paths.

93. A medical device comprising:
- a proximal handle;
- an elongated member having a proximal end, a distal end, and a lumen therebetween, the proximal end being coupled to the proximal handle, the elongated member being sufficiently flexible to traverse through tortuous anatomy of a patient's body;
- an end effector proximate the distal end of the elongated member, actuation of the proximal handle causing the end effector to perform a medical procedure; and
- a distal member configured to open and substantially close the distal end of the lumen, the distal member defining a flow path such that, when the distal member substantially closes the distal end of the lumen, the flow path enables a flow communication between the lumen and an outside of the elongated member,
- wherein the flow path comprises an inlet and a plurality of outlets connecting to the inlet.

94. The device of claim 93, wherein the end effector comprises a tissue cutting end effector.

95. The device of claim 94, wherein the end effector consists essentially of a snare loop.

* * * * *